United States Patent [19]

Furukawa et al.

[11] Patent Number: 4,996,147
[45] Date of Patent: Feb. 26, 1991

[54] PROCESS FOR PRODUCING L-THREONINE BY FERMENTATION

[75] Inventors: Satoru Furukawa; Toshihide Nakanishi, both of Hofu, Japan

[73] Assignee: Kyowa Hakko Kogyo Co., Ltd., Tokyo, Japan

[21] Appl. No.: 225,385

[22] Filed: Jul. 28, 1988

[30] Foreign Application Priority Data

Jul. 31, 1987 [JP] Japan .................. 62-192303

[51] Int. Cl.$^5$ .................. C12P 13/08; C12P 15/00; C12N 1/20
[52] U.S. Cl. .................. 435/115; 435/172.1; 435/252.8; 435/849
[58] Field of Search .................. 435/115, 172.1, 849, 435/170, 252.8

[56] References Cited

U.S. PATENT DOCUMENTS 3,622,435  11/1971  Akeyama .................. 435/115

FOREIGN PATENT DOCUMENTS 1010037  3/1981  Japan .................. 435/115
0180597  9/1985  Japan .................. 435/115

OTHER PUBLICATIONS

Cohen, G., In Amino Acids: Biosynthesis and Genetic Regulation, Addison Wesley, 1983, pp. 147–158.
Lynn et al., id., pp. 173–185.
Sikyta, B., Methods in Industrial Microbiology, 1983, pp. 238–239.

Primary Examiner—Elizabeth C. Weimar
Assistant Examiner—Irene Marx
Attorney, Agent, or Firm—Antonelli, Terry, Stout & Kraus

[57] ABSTRACT

A process is disclosed for producing L-threonine, the process involves culturing in a medium a microorganism belonging to the genus Escherichia and having resistance to rifampicin, lysine, methionine, aspartic acid and homoserine, accumulating L-threonine in the culture and recovirng L-threonine therefrom.

3 Claims, No Drawings

PROCESS FOR PRODUCING L-THREONINE BY FERMENTATION

CROSS-REFERENCES TO RELATED APPLICATIONS

In commonly owned U.S. patent application Ser. No. 013,797, filed Feb. 12, 1987, a process using a microorganism belonging to the genus Escherichia which has resistance to at least one of rifampicin, lysine, methionine, aspartic acid and homoserine, or a decreased ability to degrade L-threonine is described (Japanese Patent Application No. 33693/87, EP-A-0 237 819).

BACKGROUND OF THE INVENTION

This invention relates to a process for producing L-threonine using a microorganism belonging to the genus Escherichia and having resistance to rifampicin, lysine, methionine, aspartic acid and homoserine and an ability to produce L-threonine. L-threonine is not only useful as medicaments such as amino acid preparation, etc., but also utilizable as an additive for animal feed.

Heretofore, various processes for producing L-threonine by fermentation have been known; for example, a process using a microorganism belonging to the genus Escherichia and having a borrelidin sensitivity (Japanese Published Examined Patent Application No. 6752/76), a process using a microorganism belonging to the genus Escherichia which requires diaminopimelic acid and methionine for growth and of which threonine biosynthesis system is resistant to the feedback inhibition of threonine (Japanese Published Examined Patent Application No. 10037/81), a process using a microorganism belonging to the genus Serratia which is deficient in threonine dehydrogenase and resistant to threonine metabolic antagonist (Japanese Published Examined Patent Application No. 48195/77), a process using a microorganism belonging to the genus Corynebacterium and having resistance to α-amino-β-hydroxyvaleric acid and S-(2-aminoethyl)-L-cysteine, and a requirement for methionine (Japanese Published Unexamined Patent Application No. 19087/72), a process using a microorganism belonging to the genus Brevibacterium and having resistance to α-amino-β-hydroxyvaleric acid and S-(2-aminoethyl)-L-cysteine and a requirement for leucine (Japanese Published Unexamined Patent Application No. 31093/75), a process using a microorganism belonging to the genus Brevibacterium and having resistance to α-amino-β-hydroxyvaleric acid and S-(2-aminoethyl)-L-cysteine and requirements for L-isoleucine and L-lysine (Japanese Published Unexamined Patent Application No. 224684/83), etc.

SUMMARY OF THE INVENTION

According to the present invention, L-threonine can be produced in high yield and at low cost by using a microorganism belonging to the genus Escherichia and having both an ability to produce L-threonine and resistance to rifampicin, lysine, methionine, aspartic acid and homoserine.

DETAILED DESCRIPTION OF THE INVENTION

The present invention provides a process for producing L-threonine by fermentation, which comprises culturing in a medium a microorganism belonging to the genus Escherichia and having resistance to rifampicin, lysine, methionine, aspartic acid and homoserine, and an ability to produce L-threonine until L-threonine is accumulated in the culture, and recovering L-threonine therefrom.

Any microorganism can be used in the present invention, so long as it belongs to the genus Escherichia and has resistance to rifampicin, lysine, methionine, aspartic acid and homoserine and an ability to produce L-threonine.

Strains resistant to rifampicin, lysine, methionine, aspartic acid and homoserine can be obtained by endowing an L-threonine-producing microorganism of the genus Escherichia with the aforementioned resistance properties in turn in accordance with a conventional mutation technique. The order of endowment of the resistance properties need not be arranged and any resistance property can precede other resistance properties. A preferable example is Escherichia coli H-4581. L-threonine-producing microorganisms of the genus Escherichia have such an advantage as less production of by-product amino acids.

A specific example of obtaining the above-mentioned resistant strain is given below:

Escherichia coli H-4257 (FERM BP-984) (having a diaminopimelic acid-requirement, a methionine-requirement, an α-amino-β-hydroxyvaleric acid-resistance and a decreased ability to degrade L-threonine) is subjected to a conventional mutation treatment with N-methyl-N'-nitro-N-nitrosoguanidine (NTG) (200 μg/ml, 30° C., 30 minutes) and then smeared on a 20 minimum medium [0.5% glucose, 0.1% $(NH_4)_2SO_4$, 0.2% $KH_2PO_4$, 0.7% $K_2HPO_4$, 0.1 g/l $MgSO_4.7H_2O$, 20 mg/l $Fe_2(SO_4)_3$, 50 mg/l diaminopimelic acid, 50 mg/l methionine and 2% agar, pH 7.2] containing 100 μg/ml rifampicin and cultured at 30° C. for 2 to 6 days to obtain colonies of rifampicin-resistant mutants growable thereon. Then, 50 mutant strains are picked up and subjected to the L-threonine product test to select the strain having the best L-threonine productivity. The strain is subjected to the same mutation treatment as described above, and smeared on the same minimum medium as mentioned above except that 15 g/l lysine is contained instead of rifampicin. Culturing is carried out in the same way as mentioned above to obtain colonies of lysine-resistant mutants growable thereon. From among the colonies, 50 mutant strains are picked up and subjected to the L-threonine production test. With the strain having the best L-threonine productivity, the series of steps from the mutation treatment to the L-threonine production test are repeated three times, substituting 15 g/l each of methionine, homoserine and aspartic acid in turn for lysine. The H-4581 strain thus selected as rifampicin-, lysine-, methionine-, homoserine- and aspartic acid-resistant mutant, has been deposited with the Fermentation Research Institute, Agency of Industrial Science and Technology, Japan since July 16, 1987 with access number FERM BP-1411. The depository is located at 1-3, Higashi 1 chome, Tsukuba-shi, Ibaraki-ken 305, Japan.

L-threonine can be obtained by culturing the above microorganism in a synthetic medium or a natural medium containing carbon sources, nitrogen sources, inorganic salts, growth factors and the like until L-threonine is accumulated in the culture, and recovering L-threonine therefrom.

As the carbon sources, carbohydrates such as glucose, fructose, molasses, starch hydrolyzate, etc., and organic acids such as acetic acid, propionic acid, formic acid, fumaric acid, malic acid, etc. can be used.

As the nitrogen sources, ammonia, ammonium salts of inorganic or organic acids such as ammonium chloride, ammonium 20 sulfate, ammonium acetate, ammonium phosphate, amines, other nitrogen-containing compounds, peptones, meat extract, corn steep liquor, casein hydrolyzate, soybean cake hydrolyzate, various fermentation cells and their digested products, etc. can be used.

As the inorganic compounds, potassium dihydrogenphosphate, dipotassium hydrogenphosphate, magnesium phosphate, magnesium sulfate, sodium chloride, ferrous sulfate, manganese sulfate, copper sulfate, calcium carbonate, etc. can be used.

Culturing is carried out under aerobic conditions by shaking culture or agitation submerged culture or the like at a temperature of 20° to 40° C., preferably 28° to 38° C. The pH of the medium is in the range of 5 to 9, and is preferably maintained at around neutrality. The pH is adjusted with calcium carbonate, inorganic or organic acids, alkaline solutions, ammonia, pH buffer solutions, or the like. L-threonine can be accumulated in the culture after 2 to 7 days of culturing. After the completion of culturing, precipitates such as cells, etc. are removed from the culture by means of centrifugation, etc. and L-threonine can be recovered therefrom by simultaneous application of ion exchange treatment, concentration, salting-out or the like.

The present invention is illustrated by the following Examples.

EXAMPLE 1

L-threonine production test was carried out using *Escherichia coli* H-4581 (FERM BP-1411) as the seed strain.

H-4581 strain was cultured with shaking at 30° C. for 16 hours in a seed medium (pH 7.4) comprising 2% glucose, 1% peptone, 1% yeast extract, 0.25% NaCl and 0.1 g/l diaminopimelic acid. 100 ml of the thus obtained seed culture was inoculated into a 2l-small fermentor containing 1l of the following fermentation medium and cultured at 30° C. with stirring at 700 rpm and an aeration rate of 1 vvm of 80 hours while supplying the fermentation medium with 60% glucose where appropriate, and adjusting the pH to 6.5 with aqua ammonia during culture. L-threonine was produced in an amount of 70.5 g/l. Where the parent strain H-4257 (FERM BP-984) was likewise cultured as a control, L-threonine was produced in an amount of 48.1 g/l.

The fermentation medium has the following composition:
Glucose: 3%
$(NH_4)_2SO_4$: 1.2%
$KH_2PO_4$: 0.3%
$MgSO_4.7H_2O$: 0.02%
Diaminopimelic acid: 0.6 g/l
DL-methionine: 0.1 g/l
Corn steep liquor: 1.2%

One liter of the L-threonine-containing fermentation broth obtained by the use of H-4581 strain was then subjected to centrifugation (3000 rpm, 10 minutes) to remove the cells and other impurities therefrom. The thus obtained supernatant was passed through a column of strongly acidic ion exchange resin, Diaion SK I (H+-type, product of Mitsubishi Kasei Corporation, Japan) to adsorb L-threonine thereon. After the column was washed with water, the column was subjected to elution with 0.5N aqueous ammonia to collect L-threonine fractions. The collected fractions were concentrated, and ethanol was added thereto. The mixture was stored under cooling to give 48.9 g of L-threonine crystals having a purity of 98% or higher.

EXAMPLE 2

The H-4581 strain which was used as seed strain was cultured with shaking at 30° C. for 16 hours in a seed medium (pH 7.4) comprising 2% glucose, 1% peptone, 1% yeast extract, 0.25% NaCl and 0.1 g/l diaminopimelic acid. Then, 2 ml of the seed culture thus obtained was inoculated into a 250 ml-Erlenmeyer flask containing 20 ml of the above-mentioned fermentation medium, and cultured with shaking at 30° C. for 72 hours. L-threonine was produced in an amount of 22.1 g/l. Where the parent strain H-4257 was likewise cultured as a control, L-threonine was produced in an amount of 17.2 g/l.

What is claimed is:

1. A process for producing L-threonine by fermentation which comprises culturing in a medium *Escherichia coli* FERM BP-1411 having resistance to rifampicin, lysine, methionine, aspartic acid and homoserine and an ability to produce L-threonine, until L-threonine is accumulated in the culture, and recovering L-threonine therefrom.

2. A process according to claim 1, wherein said culturing is conducted at 20° to 40° C. for 2 to 7 days.

3. A biologically pure culture of the microorganism *Escherichia coli* having all of the identifying characteristics of FERM BP-1411, which culture possesses an ability to produce L-threonine.

* * * * *